United States Patent [19]

Sloboda

[11] 4,325,949

[45] Apr. 20, 1982

[54] COMBINATIONS OF AGENTS WHICH GIVE ENHANCED ANTI-INFLAMMATORY ACTIVITY

[75] Inventor: Adolph E. Sloboda, New City, N.Y.

[73] Assignee: American Cyanamid Company, Stamford, Conn.

[21] Appl. No.: 219,750

[22] Filed: Dec. 23, 1980

Related U.S. Application Data

[63] Continuation of Ser. No. 121,851, Feb. 15, 1980, abandoned.

[51] Int. Cl.³ ............... A61K 31/60; A61K 31/275; A61K 31/615

[52] U.S. Cl. .................................. 424/230; 424/233; 424/304

[58] Field of Search .................. 424/230, 233, 304

[56] References Cited

PUBLICATIONS

Chem. Abst.-69-100208s (1968).

Primary Examiner—Stanley J. Friedman
Attorney, Agent, or Firm—Edward A. Conroy, Jr.

[57] ABSTRACT

This disclosure describes compatible additive anti-inflammatory compositions comprising certain novel antiarthritic agents and the known non-steroidal anti-inflammatory agents.

5 Claims, No Drawings

COMBINATIONS OF AGENTS WHICH GIVE ENHANCED ANTI-INFLAMMATORY ACTIVITY

CROSS REFERENCE TO RELATED APPLICATION

This application is a continuation of my copending application Ser. No. 121,851, filed Feb. 15, 1980, now abandoned.

BRIEF SUMMARY OF THE INVENTION

This invention relates to new and useful combinations of non-steroidal anti-inflammatory agents and certain anti-arthritic (and also anti-inflammatory) agents and their tautomeric forms which may be represented by the following structural formulae:

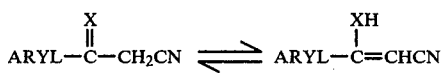

wherein X is oxo (=O) or imino (=NH) and ARYL is 2-thienyl, 3-thienyl, or a moiety of the formula:

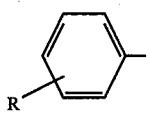

wherein R is hydrogen or fluoro with the proviso that R may not be ortho-fluoro when X is imino. Also included within the purview of the present invention are the pharmacologically acceptable cationic salts of the above-defined anti-arthritic agents when X is oxo. Such useful pharmaceutically acceptable salts are those with pharmacologically acceptable metal cations. Preferred metal cations are those derived from the alkali metals, e.g. lithium, sodium and potassium, and from the alkaline earth metals, e.g. magnesium and calcium, although cationic forms of other metals, e.g. aluminum, zinc, iron and in particular copper, are within the scope of the invention.

The non-steroidal anti-inflammatory agents operable in the novel compositions of the present invention are those which are prostaglandin synthetase inhibitors and include the following:

ASPIRIN®; 2-(acetyloxy)benzoic acid.
INDOMETHACIN®; 1-(4-chlorobenzoyl)-5-methoxy-2-methyl-1H-indole-3-acetic acid.
PHENYLBUTAZONE®; 4-butyl-1,2-diphenyl-3,5-pyrazolidenedione.
FENBUFEN®; γ-oxo-(1,1'-biphenyl)-4-butanoic acid.
ALCOFENAC®; 3-chloro-4-(2-propenyloxy)-benzeneacetic acid.
AZAPROPAZONE®; 5-(dimethylamino)-9-methyl-2-propyl-1H-pyrazolo[1,2-a][1,2,4]benzotriazine-1,3(2H)-dione.
DECLOFENAC® SODIUM; sodium 2-[(2,6-dichlorophenyl)amino]benzeneacetate.
FENCLOZIC ACID®; 2-(4-chlorophenyl)-4-thiazoleacetic acid.
FENOPROFEN®; α-methyl-3-phenoxybenzeneacetic acid.
FLUPROFEN®; 3'-fluoro-α-methyl-(1,1'biphenyl)-4-acetic acid.
FLUFENAMIC ACID®; 2-[3-(trifluoromethyl)-phenyl]aminobenzoic acid.
FLURBIPROFEN®; 2-fluoro-α-methyl-(1,1'-biphenyl)-4-acetic acid.
IBUPROFEN®; α-methyl-4-(2-methylpropyl)-benzeneacetic acid.
IBUFENAC®; 4-(2-methylpropyl)-benzeneacetic acid.
ISOXICAN®; 4-hydroxy-2-methyl-N-(5-methyl-3-isoxazolyl)-2H-1,2-benzothiazine-3-carboxamide, 1,1-dioxide.
KETOPROFEN®; 3-benzoyl-α-methyl-benzeneacetic acid.
FLUFENISAL®; 4-(acetyloxy)-4'-fluoro-(1,1'-biphenyl)-3-carboxylic acid.
SULINDAC®; 5-fluoro-2-methyl-1-[4-(methylsulfinyl)phenyl]methylene-1H-indene-3-acetic acid.
METIAZINIC ACID®; 10-methyl-10H-phenothiazine-2-acetic acid.
NAPROXEN®; 5-methoxy-α-methyl-2-naphthaleneacetic acid.
OXYPHENBUTAZONE®; 4-butyl-1-(p-hydroxyphenyl)-2-phenyl-3,5-pyrazolidinedione.
PIRPROFEN®; 3-chloro-4-(2,5-dihydro-1H-pyrrol-1-yl)-α-methyl-benzeneacetic acid.
TOLEMETIN®; 1-methyl-5-(4-methylbenzoyl)-1H-pyrrole-2-acetic acid.
CICLOPROFEN®; α-methyl-9H-fluorene-2-acetic acid.
CLONIXIN®; 2-[(3-chloro-2-methylphenyl)amino]-3-pyridinecarboxylic acid.
KETOPHENYLBUTAZONE®; 4-(3-oxobutyl)-1,2-diphenyl-3,5-pyrazolidinedione.
FUROBUFEN®; γ-oxo-2-dibenzofuranbutanoic acid.
INDOPROFEN®; 4-(1,3-dihydro-1-oxo-2H-isoindol-2-yl)-α-methyl-benzeneacetic acid.
CLIPROFEN®; 3-chloro-α-methyl-4-(2-thienylcarbonyl)benzeneacetic acid.
DIFLUNISAL®; 5-(2,4-difluorophenyl)salicylic acid.
FENCLORAC®; α,m-dichloro-p-cyclohexylphenylacetic acid.
FENOPROFEN® CALCIUM; calciumα-methyl-3-phenoxybenzeneacetate.
MECLOFENAMIC ACID®; N-(2,6-dichloro-m-tolyl)anthranilic acid.
OXAPROZIN®; 4,5-diphenyl-2-oxazolepropionic acid.
SUPROFEN®; α-methyl-4-(2-thienylcarbonyl)benzeneacetic acid.
PIROXICAN®; 4-hydroxy-2-methyl-N-2-pyridimyl-2H-1,2-benzothiazine-3-carboxamide-1,1-dioxide.
MECLOMEN®; N-(2,6-dichloro-m-tolyl)anthranilic acid, monosodium salt.

DETAILED DESCRIPTION OF THE INVENTION

The generally used non-steroidal anti-inflammatory agents operable in the novel compositions of the present invention exhibit the phenomenon known as drug interference or drug antagonism. That is, the anti-inflammatory effect of one drug may interfere with the anti-inflammatory effects of the second drug of the combination. As a result the activity of the combination of the two drugs will never attain the algebraic sum of the individual actions. It has now been discovered that the combination of an anti-inflammatory (antiarthritic) agent as hereinabove defined on page 1 and a known non-steroidal anti-inflammatory agent unexpectedly produces a true additive anti-inflammatory effect.

A distinct advantage of the present invention lies in the wide range in which the anti-inflammatory agents may be employed and still retain additivity. For example, the proportion of the hereinabove defined anti-arthritic agent to the non-steroidal anti-inflammatory agent may range from 100:1 to 1:100 parts by weight although the preferred range is not quite so wide and varies from 5:1 to 1:5 parts by weight. The novel additive compositions of the present invention have thus been found to be highly useful for amelio-rating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the additive compositions for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the novel compositions may be administered in any convenient manner such as by the oral, intravenous, intramuscular, topical, intra-articular or subcutaneous routes.

Compositions according to the present invention having the desired clarity, stability and adaptability for parenteral and intra-articular use are obtained by dissolving from 0.10% to 10.0% by weight of the combination in a vehicle consisting of a polyhydric aliphatic alcohol or mixtures thereof. Expecially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of the combination dissolved in the above vehicle may vary from 0.10 to 10.0% by weight, it is preferred that the amount employed be from about 3.0 to about 9.0% by weight. Although various mixtures of the arorementioned non-volatile polyethylene glycols may be employed, it is preferred to use a mixture having an average molecular weight of from about 200 to about 400.

In addition to the active compositions, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-$\alpha$-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active composition is 0.25 to 0.05 mg./ml. of the finished compositions. They are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory. For intra-articular use for large joints such as the knee, from about two to about 20 mg. per joint per week may be used, with proportionally smaller doses for smaller joints.

The additive combinations of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the compositions may be incorporated with excipients and used in the form of tablets, troches, capsules, elixirs, suspensions, syrups, wafers, and the like. Such compositions and preparation should contain at least 0.1% of active ingredients. The percentage of the compositions and preparations may, of course, be varied and may conveniently be between about 2% to about 60% of the weight of the unit. The amount of active ingredients in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compounds, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The anti-inflammatory activity of the novel additive compositions of the present invention was demonstrated in the adjuvant induced arthritis test in the rat as follows. Groups of three Royal Hart, Wistar strain rats, weighing 200±10 g. each were injected intradermally in the right hind paw with Freund's adjuvant (dried human tubercle bacilli in a mineral oil vehicle) at a dose of 2 mg./kg. of body weight. Test compositions were administered orally in a 1.5% starch vehicle at various doses once daily on days 0 through 13 post challenge. Control rats were treated in a similar manner, but given only starch vehicle. On the 14th, 21st, 28th and 35th days post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24, where 0 represents a complete absence of induced arthritic modules and 24 represents the maximum degree of inflammation. The mean grade for each treated group is calculated and the effects of each test compound are expressed as percent inhibition of the control grade. The following Tables I–V record the results of tests conducted with the compositions of this invention and conventional anti-inflammatory agents both separately and in combination. All tests were replicated several times. Each treatment group represents a total of 18 rats. Each challenged control group comprised 36 rats and each unchallenged control group was 9 rats.

TABLE I

The Effect of Combining Benzoylacetonitrile and Indomethacin in the Treatment of Adjuvant Arthritis

| Drug Dose (mg./kg.) | | Body Weight Gain in Grams Day | | Primary Lesions (% Inhibition) Day | | Secondary Lesions (% Inhibition) Day | |
|---|---|---|---|---|---|---|---|
| Benzoyl-acetonitrile | Indo-methacin | 14 | 21 | 14 | 21 | 14 | 21 |
| Normal Rats | | 83 | 111 | — | — | — | — |
| Adjuvant Controls | | 40 | 29 | 0 | 0 | 0 | 0 |
| 100 | — | 56* | 79* | 55* | 54* | 76* | 56* |
| 50 | — | 58* | 62* | 60* | 45* | 66* | 43* |
| 25 | — | 57* | 57* | 36* | 24 | 50* | 17 |
| — | 1.0 | 76* | 70* | 57* | 24 | 48* | 27 |
| — | 0.5 | 61* | 51* | 41* | 8 | 11 | 3 |
| — | 0.25 | 43 | 46 | 44* | 19 | 25 | 22 |
| 100 | 1.0 | 70* | 87* | 86* | 76* | 78* | 69* |
| 50 | 0.5 | 63* | 89* | 77* | 74* | 75* | 66* |

TABLE I-continued

The Effect of Combining Benzoylacetonitrile and Indomethacin in the Treatment of Adjuvant Arthritis

| Drug Dose (mg./kg.) | | Body Weight Gain in Grams Day | | Primary Lesions (% Inhibition) Day | | Secondary Lesions (% Inhibition) Day | |
|---|---|---|---|---|---|---|---|
| Benzoyl-acetonitrile | Indo-methacin | 14 | 21 | 14 | 21 | 14 | 21 |
| 25 | 0.25 | 67* | 74* | 62* | 50* | 59* | 41* |

*Significantly greater than adjuvant controls. $p = <.05$ by t test

TABLE II

The Effect of Combining Benzimidoylacetonitrile and Indomethacin in the Treatment of Adjuvant Arthritis

| Drug Dose (mg./kg.) | | Body Weight Gain in Grams Day | | Primary Lesions (% Inhibition) Day | | Secondary Lesions (% Inhibition) Day | |
|---|---|---|---|---|---|---|---|
| Benzimi-doylace-tonitrile | Indo-methacin | 14 | 21 | 14 | 21 | 14 | 21 |
| Normal Rats | | 123 | 148 | — | — | — | — |
| Adjuvant Controls | | 47 | 27 | 0 | 0 | 0 | 0 |
| 100 | — | 70* | 88* | 68* | 55* | 75* | 34* |
| 50 | — | 77* | 80* | 68* | 58* | 70* | 43* |
| 25 | — | 72* | 66* | 56* | 33* | 63* | 24* |
| — | 1.0 | 92* | 84* | 63* | 27 | 54* | 30* |
| — | 0.5 | 71* | 57* | 50* | 8 | 32* | 10 |
| — | 0.25 | 59 | 45 | 29* | 0 | 22 | 3 |
| 100 | 1.0 | 80* | 104* | 90* | 83* | 72* | 63* |
| 50 | 0.5 | 76* | 83* | 82* | 68* | 69* | 48* |
| 25 | 0.25 | 82* | 74* | 62* | 34* | 45* | 18 |

*Significantly greater than adjuvant controls. $p = <.05$ by t test.

TABLE III

The Effect of Combining Benzoylacetonitrile and Aspirin in the Treatment of Adjuvant Arthritis

| Drug Dose (mg./kg.) | | Body Weight Gain In Grams Day | | | | Primary Lesions (% Inhibition) Day | | | | Secondary Lesions (% Inhibition) Day | | | |
|---|---|---|---|---|---|---|---|---|---|---|---|---|---|
| Benzoylacetonitrile | Aspirin | 14 | 21 | 28 | 35 | 14 | 21 | 28 | 35 | 14 | 21 | 28 | 35 |
| Normal Rats | | 90 | 144 | — | — | — | — | — | — | — | — | — | — |
| Adjuvant Control | | 24 | 16 | 22 | 40 | 0 | 0 | 0 | 0 | 0 | 0 | 0 | 0 |
| 25 | — | 52* | 52* | 75* | 86* | 60* | 36* | 11 | 4 | 70* | 40* | 20* | 38* |
| 12.5 | — | 57* | 53* | 55* | 81* | 44* | 16* | 10 | 6 | 45* | 17* | 25* | 22* |
| — | 100 | 45* | 42* | 44* | 48 | 32* | 8 | 1 | 5 | 14 | 28* | 25* | 24* |
| — | 50 | 19 | 7 | 11 | 32 | 21* | 0 | 0 | 0 | 27* | 12 | 31* | 21* |
| 25 | 100 | 52* | 60* | 71* | 83* | 68* | 40* | 28* | 37* | 64* | 45* | 45* | 35* |
| 25 | 50 | 49* | 57* | 59* | 81* | 55* | 20* | 16* | 13* | 65* | 30* | 34* | 27* |
| 12.5 | 100 | 54* | 49* | 43 | 54 | 56* | 34* | 24* | 37* | 44* | 40* | 40* | 42* |
| 12.5 | 50 | 50* | 43* | 48 | 82* | 63* | 41* | 25* | 27* | 55* | 43* | 33* | 24* |

*Significantly greater than adjuvant controls. $p = <.05$ by t test

TABLE IV

The Effect of Combining (p-Fluorobenzoyl)-acetonitrile or β-Amino-2-thiopheneacrylonitrile and Aspirin in the Treatment of Adjuvant Arthritis

| Drug Dose (mg./kg.) | | | Body Weight Gain in Grams Day | | | | Primary Lesions (% Inhibition) Day | | | | Secondary Lesions (% Inhibition) Day | | | |
|---|---|---|---|---|---|---|---|---|---|---|---|---|---|---|
| β-Amino-2-thiophene-acrylonitrile | (p-Fluorobenzoyl)-acetonitrile | Aspirin | 14 | 21 | 28 | 35 | 14 | 21 | 28 | 35 | 14 | 21 | 28 | 35 |
| Normal Rats | | | 128 | 167 | — | — | — | — | — | — | — | — | — | — |
| Adjuvant Controls | | | 52 | 50 | 52 | 89 | 0 | 0 | 0 | 0 | 0 | 0 | 0 | 0 |
| — | — | 100 | 47 | 46 | 57 | 97 | 10 | 2 | 13 | 1 | 1 | 2 | 2 | 4 |
| — | — | 50 | 45 | 42 | 60 | 93 | 16* | 11 | 17* | 0 | 5 | 10 | 20 | 0 |
| — | 50 | — | 75* | 77* | 93* | 125* | 53* | 32* | 27* | 22* | 34* | 10 | 28* | 19 |
| — | 25 | — | 71* | 65 | 80* | 111* | 30* | 17* | 0 | 6 | 23* | 0 | 0 | 7 |
| — | 50 | 100 | 75* | 72* | 98* | 141* | 57* | 42* | 37* | 43* | 17 | 17 | 9 | 12 |
| — | 25 | 100 | 69* | 81* | 86* | 116* | 58* | 43* | 24* | 28* | 38* | 24* | 9 | 13 |
| — | 50 | 50 | 77* | 68* | 74* | 100 | 54* | 24* | 3 | 14 | 24* | 2 | 10 | 14 |
| — | 25 | 50 | 74* | 75* | 86* | 117* | 40* | 24* | 18* | 0 | 19 | 1 | 9 | 5 |
| 50 | — | — | 63 | 66* | 76* | 108* | 16 | 14 | 6 | 1 | 13 | 0 | 4 | 11 |
| 50 | — | 100 | 46 | 54 | 54 | 88 | 40* | 23* | 10 | 0 | 12 | 6 | 0 | 0 |

TABLE IV-continued

The Effect of Combining (p-Fluorobenzoyl)-acetonitrile or β-Amino-2-thiopheneacrylonitrile and Aspirin in the Treatment of Adjuvant Arthritis

| Drug Dose (mg./kg.) | | | Body Weight Gain in Grams Day | | | | Primary Lesions (% Inhibition) Day | | | | Secondary Lesions (% Inhibition) Day | | | |
|---|---|---|---|---|---|---|---|---|---|---|---|---|---|---|
| β-Amino-2-thiophene-acrylonitrile | (p-Fluorobenzoyl)-acetonitrile | Aspirin | 14 | 21 | 28 | 35 | 14 | 21 | 28 | 35 | 14 | 21 | 28 | 35 |
| 50 | — | 50 | 70* | 96* | 102* | 143* | 58* | 35* | 32* | 26 | 27* | 7 | 10 | 10 |

*Significantly greater than adjuvant controls. p = <.05 by t test

TABLE V

The Effect of Combining Benzoylacetonitrile and Prednisolone in the Treatment of Adjuvant Arthritis

| Drug Dose (mg./kg.) | | Body Weight Gain in Grams Day | | | | Primary Lesions (% Inhibition) Day | | | | Secondary Lesions (% Inhibition) Day | | | |
|---|---|---|---|---|---|---|---|---|---|---|---|---|---|
| Benzoylacetonitrile | Prednisolone | 14 | 21 | 28 | 35 | 14 | 21 | 28 | 35 | 14 | 21 | 28 | 35 |
| Normal Rats | | 96 | 137 | — | — | — | — | — | — | — | — | — | — |
| Adjuvant Controls | | 34 | 27 | 32 | 58 | 0 | 0 | 0 | 0 | 0 | 0 | 0 | 0 |
| 25 | — | 47 | 47* | 51* | 69 | 62* | 38* | 31* | 30* | 62* | 30* | 19 | 20* |
| 12.5 | — | 49 | 38 | 55* | 68 | 49* | 32* | 25* | 19* | 59* | 43* | 25 | 26* |
| — | 10 | 23 | 47 | 75* | 95* | 57* | 24* | 14 | 13 | 55* | 21* | 3 | 17* |
| — | 5 | 22 | 26 | 44 | 71 | 63* | 24* | 17* | 11 | 45* | 16* | 5 | 20* |
| 25 | 10 | 34 | 71* | 94* | 119* | 88* | 65* | 49* | 42* | 72* | 64* | 39* | 35* |
| 12.5 | 10 | 30 | 56* | 87* | 118* | 78* | 52* | 28* | 34* | 77* | 33* | 17 | 15 |
| 25 | 5 | 33 | 55* | 64* | 91* | 83* | 53* | 36* | 38* | 80* | 40* | 13 | 19* |
| 12.5 | 5 | 45 | 63* | 66* | 83* | 78* | 33* | 22* | 23* | 67* | 13* | 7 | 10 |

*Significantly greater than adjuvant controls. p = <.05 by t test

Adjuvant induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Pathol. 42, 73 (1963). E. M. Glenn, Am. J. Vet. Res. 27 (116), 339 (1966) has classified adjuvant induced polyarthritis as a crippling and permanent deformity resulting from diffuse connective tissue involvement around certain susceptible joints in the rat. Zahiri et al., Can. Med. Ass. J. 101, 269 (1969) have shown that the fusiform swelling of the distal joints is associated with edema, congestion and synovitis including pannus formation, all of which precede the ultimate destruction of bone and cartilage. Furthermore, Zahiri et al., indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration. See S. Wong et al., J. Pharm. & Exptl. Ther. 185, 127 (1973) and G. R. Bobalick et al., Agents & Actions 4, 364 (1974). In a similar manner, inhibition of the progress of arthritis in paws of rats treated with the compounds of this invention also lessens associated joint deterioration.

The invention will be described in greater detail in conjunction with the following specific examples.

EXAMPLE 1

Benzoylacetonitrile

The compound benzoylacetonitrile may be prepared as described by Dorsch, et al., J.A.C.S., 54, 2960 (1932).

EXAMPLE 2

(p-Fluorobenzoyl)-acetonitrile

The compound (p-fluorobenzoyl)-acetonitrile may be prepared as described by Pihl. et al., Reakts, Sposobnost Org. Soedin. Tartu. Gos. Unit., 5(1), 27 (1968).

EXAMPLE 3

(o-Fluorobenzoyl)-acetonitrile

The compound (o-fluorobenzoyl)-acetonitrile may be prpeared as described by M. Nakanishi, et al., J. Med. Chem., 16(3), 214–219 (1973).

EXAMPLE 4

(m-Fluorobenzoyl)-acetonitrile

The compound (m-fluorobenzoyl)-acetonitrile may be prepared as described by Pihl, et al., Reakts. Sposobnost Org. Soedin. Tartu. Gos. Unit., 5(1), 27 (1968).

EXAMPLE 5

β-Oxo-2-thiophenepropionitrile

This compound may be prepared as described in U.S. Pat. No. 2,540,982.

EXAMPLE 6

β-Amino-3-thiopheneacrylonitrile

A 500 ml., three-necked flask is equipped with a mechanical stirrer, gas inlet, dry ice condenser, potassium hydroxide drying tube and addition funnel. A 100 ml. portion of ammonia is condensed into the flask and a pellet of sodium is added. When the dark blue colors persists, ferric chloride is added discharging the color to brown. A 3.2 g. portion of sodium is added and the mixture is allowed to stand for 45 minutes. A 5.7 ml. portion of acetonitrile in 10 ml. of tetrahydrofuran is added and the reaction is stirred for 20 minutes. The reaction is cooled in a dry ice-acetone bath and 10.9 g. of 3-thiophenecarbonitrile in 25 ml. of tetrahydrofuran is added. The reaction is stirred in the cold bath for 90 minutes and then heated at reflux for 3 hours. A 7.4 g. portion of ammonium chloride is added and the mixture is allowed to evaporate overnight. A 100 ml. portion of water and 100 ml. of chloroform are added and the mixture is filtered. The aqueous phase is extracted with chloroform, the combined organic solution is washed once with water, dried over magnesium sulfate and filtered through Magnesol. The filtrate is evaporated in vacuo to an orange oil. A 30 ml. portion of benzene is added and then petroleum ether until the mixture is cloudy. Cooling produces a precipitate which is collected and recrystallized from benzene giving the desired product as a solid, mp. 67°–69.5° C.

EXAMPLE 7

β-Oxo-3-thiophenepropionitrile

A 1.2 g. portion of β-amino-3-thiopheneacrylonitrile is added to 10 ml. of 1 N hydrochloric acid. A 40 ml. portion of methanol is added and the mixture is stirred for 3 hours. The mixture is evaporated in vacuo to a residue which is dissolved in 35 ml. of hot methanol and treated with charcoal. After cooling, petroleum ether is added, the mixture is filtered and the collected solid is discarded. The filtrate is evaporated and the residue is dissolved in 35 ml. of hot isopropanol and the insoluble material is filtered and discarded. The filtrate is cooled and the solid is collected giving the desired produce as white plates, mp. 87°–88° C.

EXAMPLE 8

β-Amino-2-thiopheneacrylonitrile

A reaction flask is dried by flaming with a stream of nitrogen passing through it.

About 100 ml. of ammonia is condensed in the reaction flask and a small piece of sodium is added, giving a blue color. The color is discharged with ferric chloride and 2.7 g. of sodium is added. When the blue color disappears, 4.91 ml. of acetonitrile in 10 ml. of ether is added. The reaction is cooled in a dry ice-acetone bath and 9.28 g. of 2-thiophenecarbonitrile in 25 ml. of tetrahydrofuran is added dropwise. Cooling is continued for 30 minutes, then the ammonia and solvent are allowed to evaporate. A 50 ml. portion of water is added and the mixture is extracted with methylene chloride. The methylene chloride extracts are dried over sodium sulfate and then passed through Magnesol. Hexanes are added and the filtrate is evaporated on a steam bath to an oil. The oil is dry column chromatographed on silica gel, eluting with methylene chloride. The fraction containing the desired product is taken up in methylene chloride, passed through Magnesol and the filtrate is evaporated on a steam bath with the addition of hexanes until an oil comes out. Cooling and seeding gives the desired product as crystals, mp. 50°–45° C.

EXAMPLE 9

Benzimidoylacetonitrile

The compound benzimidoylacetonitrile may be prepared as described in Chemical Abstracts, 62, 10366H (1965). It is also commercially available from Aldrich Chemical Company.

EXAMPLE 10 p-Fluorobenzimidoylacetonitrile

The compound p-fluorobenzimidoylacetonitrile may be prepared as described by Lang, et al., J. Med. Chem., 18, 441 (1975).

EXAMPLE 11 m-Fluorobenzimidoylacetonitrile

A 1.21 g. portion of m-fluorobenzonitrile, 0.52 ml. of acetonitrile, 0.5 g. of sodium hydride and 0.1 ml. of t-butanol are added to 25 ml. of ether. The mixture is refluxed on a steam bath for one hour. Methanol and water are added. The layers are separated and the aqueous layer is extracted with two 25 ml. portions of ether. The combined ether layers are dried over sodium sulfate, passed through diatomaceous earth, diluted with hexanes and evaporated on a steam bath. The resulting oil is chromatographed using methylene chloride on silica gel giving 0.52 g. of an oil which crystallizes. This material is taken up in methylene chloride. Hexanes are added and the mixture is evaporated, giving an oil with crystallizes. This material is recrystallized from carbon tetrachloride giving the desired product, mp. 67°–68° C.

EXAMPLE 12

Preparation of 50 ml. Tablets

| Per Tablet | |
| --- | --- |
| 0.050 g. | Benzoylacetonitrile |
| 0.324 g. | Aspirin ® |
| 0.080 g. | Lactose |
| 0.010 g. | Corn starch (for mix) |
| 0.008 g. | Corn starch (for paste) |
| 0.472 g. | |
| 0.002 g. | Magnesium stearate (1%) |
| 0.474 g. | |

The benzoylacetonitrile, aspirin, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dried granules are passed through a No. 16 screen. The mixture is lubricated with 1% magnesium stearate and compressed into tablets.

EXAMPLE 13

Preparation of Oral Syrup

| Ingredient | Amount |
| --- | --- |
| (p-Fluorobenzoyl)-acetonitrile | 500 mg. |
| Indomethacin ® | 100 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the (p-fluorobenzoyl)-acetonitrile and indomethacin are suspended therein. The saccharin, sodium benzoate, flavor and dye are added and dissolved. The volume is adjusted to 100 ml. with distilled water. Each ml. of syrup contains 5 mg. of (p-fluorobenzoyl)-acetonitrile and one mg. of indomethacin.

EXAMPLE 14

Preparation of Hard Shell Capsule

| Ingredient | mg./Capsule |
|---|---|
| β-Amino-2-thiopheneacrylonitrile | 500 |
| Phenylbutazone ® | 5 |
| Lactose, Spray dried | qs |
| Magnesium stearate | 5 |

The components are blended and filled in hard shell capsules.

EXAMPLE 15

Preparation of Parenteral Solution

In a solution of 700 ml. of propylene glycol and 200 ml. of water for injection is suspended 20.0 grams of benzimidoylacetonitrile and 20.0 grams of Naproxen ® with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of active ingredients and sealed under nitrogen.

EXAMPLE 16

Preparation of Topical Cream

| Ingredient | Amount |
|---|---|
| Benzoylacetonitrile | 1.0% |
| Fenbufen | 1.0% |
| Ethoxylated stearyl alcohol | 10.0% |
| Benzyl alcohol | 0.9% |
| Isopropyl palmitate | 5.0% |
| Glycerin | 5.0% |
| Sorbitol solution (USP) | 5.0% |
| Lactic acid qs. to pH 4.0-5.0 | |
| Water qs. to | 100.0% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°-75° C. The m-fluorobenzimidoylacetonitrile and Fenbufen are added to the wax phase and the mixture is stirred until a clear solution is obtained. The benzyl alcohol is added and dissolved in the wax phase while maintaining agitation. Both phases are kept at about the same temperature during transfer. The mixture is cooled while agitation is continued. At a temperature of 50°-55° C. the balance of the water is added. The pH is adjusted to 4.0-5.0 with lactic acid. The batch is cooled with minimum agitation until the cream sets in its final form.

EXAMPLE 17

Preparation of Intra-articular Product

| Ingredient | Amount |
|---|---|
| p-Fluorobenzoylacetonitrile | 2-20 mg. |
| Oxyphenbutazone ® | 10-20 mg. |
| NaCl (physiological saline) | 0.9% |
| Benzyl alcohol N.F. | 0.9% |
| Sodium carboxymethylcellulose | 1-5% |
| pH adjusted to 5.0-7.5 | |
| Water for injection qs ad | 100% |

EXAMPLE 18

Preparation of Injectable Depo Suspension

| Ingredient | % W/V |
|---|---|
| p-Fluorobenzoylacetonitrile | 0.05-5.0 |
| Ketophenylbutazone ® | 0.10-8.0 |
| Polysorbate 80 USP | 0.2 |
| Polyethylene glycol 4000 USP | 3.0 |
| Sodium chloride USP | 0.8 |
| Benzyl alcohol N.F. | 0.9 |
| HCl to pH 6-8 | qs |
| Water for injection qs ad | 100.0 |

I claim:

1. An anti-inflammatory composition of matter comprising, in additive combination, a mixture of 2-(acetyloxy)benzoic acid and an agent of the formula:

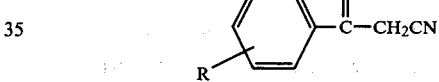

wherein X is oxo or imino and R is hydrogen or fluoro with the proviso that R may not be ortho-fluoro when X is imino, in the proportion of the 2-(acetyloxy)benzoic acid to the agent of from 100:1 to 1:100 parts by weight.

2. A composition according to claim 1 wherein X is oxo and R is para-fluoro.

3. The method of meliorating inflammation in a mammal which comprises administering to said mammal an effective amount of an anti-inflammatory composition in accordance with claim 1.

4. The method of inhibiting progressive joint deterioration in a mammal which comprises administering to said mammal an effective amount of an anti-inflammatory composition in accordance with claim 1.

5. The method of inhibiting the progression of arthritis is a mammal which comprises administering to said mammal an effective amount of an anti-inflammatory composition in accordance with claim 1.

* * * * *